(12) United States Patent
Barclay et al.

(10) Patent No.: US 9,302,215 B2
(45) Date of Patent: Apr. 5, 2016

(54) ROTARY FLUID PROCESSING SYSTEMS AND ASSOCIATED METHODS

(71) Applicant: Prometheus Technologies, LLC, Redmond, WA (US)

(72) Inventors: John A. Barclay, Redmond, WA (US); Tadeusz Szymanski, Lynnwood, WA (US); Lenard J. Stoltman, North Bend, WA (US); Kathryn Oseen-Senda, Seattle, WA (US); Hunter A. Chumbley, Bonney Lake, WA (US)

(73) Assignee: Prometheus Technologies, LLC, Redmond, WA (US)

( * ) Notice: Subject to any disclaimer, the term of this patent is extended or adjusted under 35 U.S.C. 154(b) by 28 days.

(21) Appl. No.: 14/490,592

(22) Filed: Sep. 18, 2014

(65) Prior Publication Data

US 2015/0005563 A1    Jan. 1, 2015

Related U.S. Application Data

(60) Division of application No. 13/711,575, filed on Dec. 11, 2012, now Pat. No. 8,852,328, which is a continuation of application No. 12/970,865, filed on Dec. 16, 2010, now abandoned.

(51) Int. Cl.
  *B01D 53/06* (2006.01)
  *F28F 9/26* (2006.01)
  (Continued)

(52) U.S. Cl.
  CPC . *B01D 53/06* (2013.01); *C07C 7/12* (2013.01); *F28F 9/26* (2013.01); *B01D 53/0438* (2013.01);
  (Continued)

(58) Field of Classification Search
  CPC .............. B01D 53/06; B01D 53/0438; B01D 2253/108; B01D 2256/245; B01D 2257/304; B01D 2257/504; B01D 2257/90; B01D 2259/40088; B01D 2259/4009; B01D 2259/65; C07C 7/12; F28F 9/26; Y02C 10/08; Y10T 29/4935
  USPC .............. 95/113, 148; 96/125, 126, 146, 150, 96/154; 165/86, 88
  See application file for complete search history.

(56) References Cited

U.S. PATENT DOCUMENTS 2,450,289 A  9/1948 Marek
3,087,291 A  4/1963 Stephenson
(Continued)

OTHER PUBLICATIONS

"Gas Processors Suppliers Association: Engineering Data Book (Revied Tenth Edition)" 1994, Section 25.
(Continued)

*Primary Examiner* — Frank Lawrence
(74) *Attorney, Agent, or Firm* — Chamberlain Hrdlicka

(57) ABSTRACT

Rotary fluid processing systems and associated methods are disclosed. A purification system in accordance with the particular embodiment includes a rotatable adsorbent-containing heat/mass transfer element that is generally symmetric about a rotation axis, and includes multiple radial flow paths oriented transverse to the rotation axis and multiple axial flow paths oriented transverse to the radial flow paths. The axial flow paths and radial flow paths are in thermal communication with each other, and are generally isolated from fluid communication with each other at the heat transfer element. Particular embodiments can further include a housing arrangement having multiple manifolds with individual manifolds having an entry port and an exit port, and with individual manifolds having different circumferential locations relative to the rotation axis. Still further embodiments can include a seal arrangement positioned between the heat transfer element and the housing arrangement to expose the radial flow paths, but not the axial flow paths, to the entry and exit ports of one of the manifolds, and expose the axial flow paths, but not the radial flow paths, to the entry and exit ports of another of the manifolds.

14 Claims, 13 Drawing Sheets

(51) Int. Cl.
C07C 7/12 (2006.01)
B01D 53/04 (2006.01)
(52) U.S. Cl.
CPC ..... B01D 2253/108 (2013.01); B01D 2256/245 (2013.01); B01D 2257/304 (2013.01); B01D 2257/504 (2013.01); B01D 2257/80 (2013.01); B01D 2259/4009 (2013.01); B01D 2259/40088 (2013.01); B01D 2259/65 (2013.01); Y02C 10/08 (2013.01); Y10T 29/4935 (2015.01)

(56) References Cited

U.S. PATENT DOCUMENTS

| | | |
|---|---|---|
| 3,164,452 A | 1/1965 | Westeren et al. |
| 3,594,983 A | 7/1971 | Yearout |
| 3,683,591 A | 8/1972 | Glav |
| 4,332,135 A | 6/1982 | Barclay et al. |
| 4,391,616 A | 7/1983 | Imamura |
| 4,408,463 A | 10/1983 | Barclay |
| 4,425,142 A | 1/1984 | Mann |
| 4,444,727 A | 4/1984 | Yanagihara et al. |
| 4,459,811 A | 7/1984 | Barclay et al. |
| 4,462,814 A | 7/1984 | Holmes et al. |
| 4,507,927 A | 4/1985 | Barclay |
| 4,533,372 A | 8/1985 | Valencia et al. |
| 4,553,566 A | 11/1985 | Barclay et al. |
| 4,582,516 A | 4/1986 | Kadi |
| 4,642,994 A | 2/1987 | Barclay et al. |
| 4,674,563 A | 6/1987 | Maier-Laxhuber et al. |
| 4,696,681 A | 9/1987 | LLoyd-Williams |
| 4,702,090 A | 10/1987 | Barclay et al. |
| 4,704,871 A | 11/1987 | Barclay et al. |
| 4,881,958 A | 11/1989 | Eckardt et al. |
| 4,923,493 A | 5/1990 | Valencia et al. |
| 4,956,976 A | 9/1990 | Kral et al. |
| 5,017,202 A | 5/1991 | Ogata et al. |
| 5,096,469 A | 3/1992 | Keefer |
| 5,120,338 A | 6/1992 | Potts, Jr. et al. |
| 5,120,694 A | 6/1992 | Dunne et al. |
| 5,169,414 A | 12/1992 | Panzica et al. |
| 5,182,914 A | 2/1993 | Barclay et al. |
| 5,213,593 A | 5/1993 | White, Jr. |
| 5,260,243 A | 11/1993 | Dunne et al. |
| 5,298,054 A | 3/1994 | Malik |
| 5,325,916 A | 7/1994 | Dunne et al. |
| 5,431,716 A | 7/1995 | Ebbeson |
| 5,487,775 A | 1/1996 | LaCava et al. |
| 5,503,222 A | 4/1996 | Dunne |
| 5,505,232 A | 4/1996 | Barclay et al. |
| 5,658,369 A | 8/1997 | Kusay |
| 5,693,123 A | 12/1997 | Klobucar |
| 5,702,508 A | 12/1997 | Moratalla |
| 5,733,451 A | 3/1998 | Coellner et al. |
| 6,066,192 A | 5/2000 | Toshinaga et al. |
| 6,082,133 A | 7/2000 | Barclay et al. |
| 6,155,073 A | 12/2000 | Gray |
| 6,261,345 B1 | 7/2001 | Miyano et al. |
| 6,332,323 B1 | 12/2001 | Reid et al. |
| 6,406,523 B1 | 6/2002 | Connor et al. |
| 6,467,274 B2 | 10/2002 | Barclay et al. |
| 6,478,855 B1 | 11/2002 | Okano |
| 6,630,012 B2 | 10/2003 | Wegeng et al. |
| 6,660,240 B1 | 12/2003 | Toshihiko et al. |
| 6,758,046 B1 | 7/2004 | Barclay et al. |
| 6,783,738 B1 | 8/2004 | Sasaki et al. |
| 7,022,159 B2 | 4/2006 | Kalbassi et al. |
| 7,029,647 B2 | 4/2006 | Tonkovich et al. |
| 7,141,092 B1 | 11/2006 | Roychoudhury et al. |
| 7,166,149 B2 | 1/2007 | Dunne et al. |
| 7,308,798 B2 | 12/2007 | Caggiano |
| 7,326,278 B2 | 2/2008 | Butters et al. |
| 7,569,101 B2 | 8/2009 | Hung |
| 7,744,677 B2 | 6/2010 | Barclay |
| 7,789,942 B2 | 9/2010 | Vanderstraeten et al. |
| 8,025,720 B2 | 9/2011 | Barclay |
| 8,852,328 B2 | 10/2014 | Barclay et al. |
| 2003/0037672 A1 | 2/2003 | Sircar |
| 2003/0089125 A1 | 5/2003 | Fredheim et al. |
| 2012/0152116 A1 | 6/2012 | Barclay et al. |
| 2012/0210871 A1 | 8/2012 | Barclay |

OTHER PUBLICATIONS

Agrawal et al., "Production of Medium Pressure Nitrogen by Cryogenic Air Separation," Dec. 1991, pp. 203-209, vol. 5, Butterworth-Heinemann Ltd.
Ashare, E.; Augenstein, D.C.; Yeung, J.C.; Hossan, R.J.; and Duret, G.L. "Evaluation of Systems for Purification of Fuel Gas from Anaerobic Digestion", Report to DOE contract EY-76-F-02-2991, 1978, pp. 7-31.
Barclay et al., "Purification Techniques for Natural Gas Refueling Stations," Proceedings of the 14th Natural Gas Vehicle Conference and Exhibition, Sep. 15-17, 1996, pp. 1-12.
Beysel, Dr. Gerhard, "Air Separation Plants Using Cryogenic, PSA or Membrane Technology: Development and Future Applications," International Institute of Refrigeration, Proceedings of Commission A3, Oct. 1986, pp. 65-75.
Deschamps et al., "Development of Gaseous Permeation Membranes Adapted to the Purification of Hydrocarbons," International Institute of Refrigeratoin, Proceedings of Commission A3, Oct. 1989, pp. 39-50.
Gemmingen, Ulrich V., "Pressure Swing Adsorption Process-Design and Simulation," Fundamentals of Adsorption, Proceedings of the Fourth International Conference on Fundamentals of Adsorption, May 17-22, 1992, pp. 703-712.
Haselden, G. G., "Gas Separation Fundamentals," "Gas Separation & Purification," Dec. 1989, pp. 209-215, vol. 3, Butterworth & Co. Ltd.
Holmes et al., Pilot Tests Prove Ryan/Holmes Cryogenic Acid Gas/Hydrocarbon Separations, Gas Processors Association Annual Convention Proceedings, 1982, pp. 75-85.
Keller, A.P. "Trace Constituents in Landfill Gas: Task Report on Inventory and Assessment of Cleaning Technologies", Gas Research Institute Final Report and Contract No. 5083-253-0937, Apr. 1988, pp. 14-25.
Kohl, Arther and Nielsen, Richard. Gas Purification. 5th Edition, Gulf Publishing Co., Houston, TX (1997) pp. 1022-1135.
Krauskopf et al., "Introduction to Geochemistry," 1995, pp. 142-145, McGraw-Hill, Inc.
Krich, Ken; Augenstein, Don; Batmale, John; Rutledge, Brad; Salour, Dara. Biomethane from Dairy Waste: A Sourcebook for the Production and Use of Renewable Natural Gas in California. Jul. 2005, pp. 47-69.
Optomec, "LENS Process White Paper: Fatigue Testing of LENS Ti-6-4" 2006.
Prometheus Energy, "Valveless Temperature Swing Adsorption (VTSA) Purifier for Biogas from Animal Manures" USDA- SBIR Phase I, Final Report Feb. 22, 2010.
Rautenbach et al., "Upgrading of Landfill Gas by Membranes-Process Design and Cost Evaluation," AIChE Symposium Series: Membrane Separations in Chemical Engineering, 1989, pp. 48-54, Issue 272, vol. 85.
Ryan et al., "Distillation Technology Increases Propane Recovery in Carbon-Dioxide Floods," Oil and Gas Journal, Oct. 6, 1986, pp. 62-67.
Schmidt, F.W. and Wilmot, A.J. Thermal Energy Storage and Regeneration; (Hemisphere Press, WA; 1981) pp. 279-300 and 333-349.
Wheless et al., "Trash is Your Friend: Using Landfill Gas as a Vehicle Fuel," Natural Gas Fuels, May 1996, pp. 31-36.
Yang, Ralph T., Gas Separation by Adsorption Processes. Imperial College Press, London, 1997 Edition, Chapters 1 and 6, pp. 1-235.
Younger, Dr. A. H., "Natural Gas Processing Principles and Technology", Apr. 2004, Part I, Section 7.11, pp. 7/61-7/64 Thimm Engineering, Calgary, Alberta, Canada.
Younger, Dr. A. H., "Natural Gas Processing Principles and Technology", Apr. 2004, Part II, Section 17.3, pp. 1714-17/6 Thimm Engineering, Calgary, Alberta, Canada.

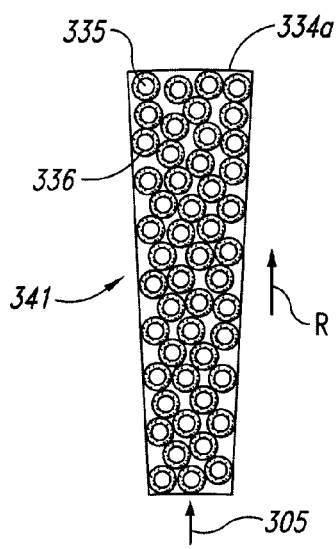 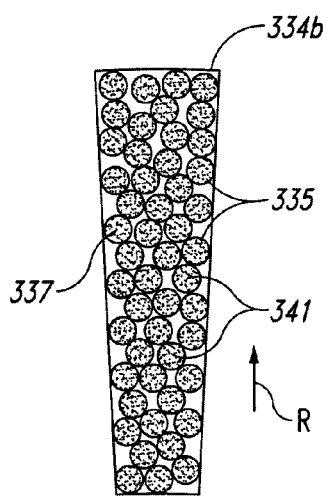 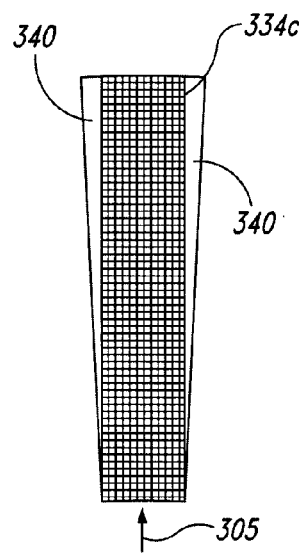
*Fig. 11A*     *Fig. 11B*     *Fig. 11C*
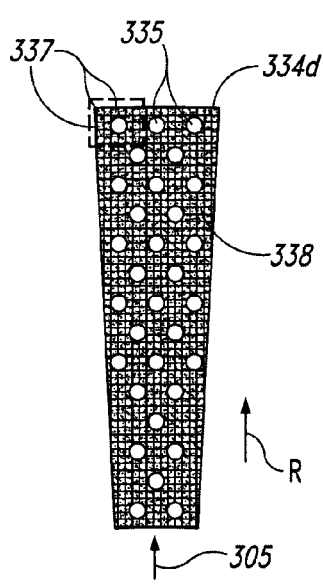 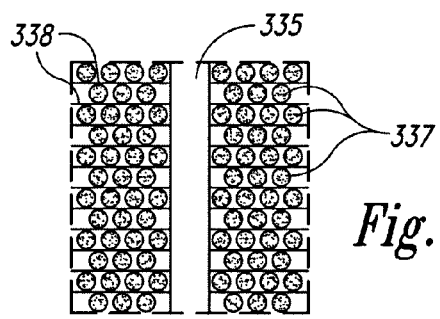
*Fig. 11E*
*Fig. 11D*
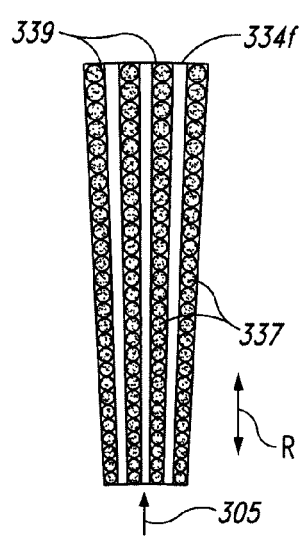 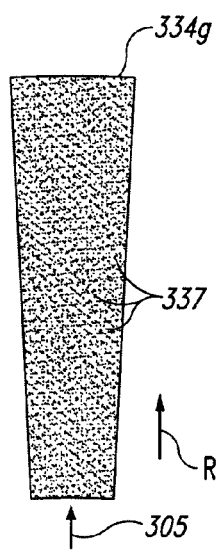
*Fig. 11F*     *Fig. 11G*

ROTARY FLUID PROCESSING SYSTEMS AND ASSOCIATED METHODS

CROSS-REFERENCE TO RELATED APPLICATIONS

This application is a divisional of U.S. application Ser. No. 13/711,575, filed on Dec. 11, 2012 and now issued as U.S. pat. No. 8,852,328, which is a continuation of U.S. application Ser. No. 12/970,865, filed on Dec. 16, 2010 and now abandoned, both of which is hereby incorporated herein by reference in its entirety for all purposes.

TECHNICAL FIELD

The present disclosure is directed generally to rotary fluid processing systems and associated methods, including rotary systems for removing impurities from methane-containing mixtures in a continuous flow process that employs limited valving.

BACKGROUND

Secure domestic energy supply, global warming and climate change are presently receiving significant scientific, business, regulatory, political, and media attention. According to increasing numbers of independent scientific reports, greenhouse gases impact the ozone layer and the complex atmospheric processes that re-radiate thermal energy into space, which in turn leads to global warming on Earth. Warmer temperatures in turn affect the entire ecosystem via numerous complex interactions that are not always well understood. Greenhouse gases include carbon dioxide, but also include other gases such as methane, which is about 23 times more potent than carbon dioxide as a greenhouse gas, and nitrous oxide, which is over 300 times more potent than carbon dioxide as a greenhouse gas.

In addition to the foregoing greenhouse gas concerns, there are significant concerns about secure domestic energy supplies, concerns that the United States imports over 60% of the crude oil it consumes from a few unstable regions of the globe, and concerns about the rate at which global oil reserves are being depleted. Accordingly, there is an increasing focus on finding alternative sources of energy, including renewable, less expensive, and domestic energy sources that are cleaner to produce and use. These sources include coal seam methane, coal mine gas, non-conventional gas from shale deposits, and stranded well gas. These energy sources also include the organic fractions of municipal solid waste, food processing wastes, animal wastes, restaurant wastes, agricultural wastes, and waste water treatment plant sludge.

Many of the foregoing organic waste streams can be converted to biogas via anaerobic bacteria to produce mixtures of methane. Examples include covered landfills where the landfill gas contains approximately 48% methane, 38% carbon dioxide, 12% nitrogen and oxygen, water vapor, and small amounts of numerous other compounds. Biogas from anaerobic digestion of organic waste streams consists of approximately 65% methane, 33% carbon dioxide, water vapor and small amounts of other compounds. Coal mine gas contains approximately 64% methane, 32% nitrogen, 3% carbon dioxide, water, and small amounts of other compounds. Non-conventional or shale gas contains approximately 90% methane, 8% ethane and propane, 2% carbon dioxide, water, and small amounts of other compounds. Stranded well gas has a wide range of compositions depending on the location but typically contains approximately 80% methane, 13% nitrogen, several percent ethane and propane, plus water and 2% carbon dioxide. These stranded or waste sources of methane are widely geographically distributed rather than in large, localized sources like a large gas field. With enhanced technology these distributed methane sources are being converted to liquid natural gas (LNG) for effective storage, transport, and distribution to industrial end users for more economical use of process heat fuel and transportation end users for economical and low emissions vehicle fuel for light and heavy duty vehicles.

The processes associated with producing both LNG and compressed natural gas from LNG (LCNG) include purifying the incoming methane gas stream to remove constituents such as those that freeze out in or otherwise degrade LNG process equipment. Among the well known purification techniques is selective adsorption of certain impurities on different adsorbents such as activated alumina or zeolites. In such adsorption techniques certain impurities in a process stream flowing within a vessel containing the adsorbent are physi-adsorbed onto the surface of the adsorbent thus removing the impurities from the process stream. This purification continues until the adsorbent is saturated. To continue purification of the process stream, the process stream must be switched to another identical vessel containing clean, cool adsorbent. This transfer between vessels is normally accomplished by opening and/or closing a combination of several valves to accomplish a semi-continuous purification of the process stream. In one type of adsorption purifier, the saturated adsorbent is heated by several hundred degrees Fahrenheit, e.g., to ~500° F., to substantially decrease the selective adsorptivity of the adsorbent. This heating thereby releases the impurities from the adsorbent so they can be purged from the vessel into a discharge stream before the clean adsorbent is cooled and prepared for another purification step. The heating, purging, and cooling steps accomplish regeneration of the adsorbent. This common type of adsorption purification is called temperature swing adsorption. It commonly involves two or more vessels in parallel which are interconnected by a complex set of control valves on the inlets and outlets of each vessel. The four stages of a temperature swing adsorption purification cycle are sequentially executed in each vessel nominally over a minimum period of several hours, e.g., 12 hours. One good application of temperature swing adsorption purification is to remove the carbon dioxide present in the methane mixtures from most of the distributed waste or stranded sources. The carbon dioxide must be efficiently removed to a concentration of about 100 parts per million to avoid freezing out in the cryogenic heat exchanger, a core component of a plant that produces LNG. The small, distributed nature of methane mixtures from many stranded gas wells, biomass waste streams or landfills makes the capital and operating costs associated with such unmonetized gas-to-LNG plants a key contribution to the delivered price of industrial process LNG fuel or LNG or LCNG vehicle fuel. Accordingly, there is a need for better purifier technology that simplifies the purification steps, provides continuous purification with fewer components such as valves, and thereby reduces capital and operating costs of such LNG plants and results in a less expensive methane fuel.

BRIEF DESCRIPTION OF THE DRAWINGS

FIGS. 11A-11G illustrate representative internal arrangements of heat transfer elements in accordance with embodiments of the disclosure.

DETAILED DESCRIPTION

Several aspects of the present disclosure are directed to rotary systems and associated methods for processing methane and other gases. Well-known characteristics often associated with certain features of these systems and methods have not been shown or described in detail to avoid unnecessarily obscuring the description of the various embodiments. Those of ordinary skill in the relevant art will understand that additional embodiments may be practiced without several of the details described below, and/or may include aspects in addition to those described below.

Several of the systems described below include a generally toroidal or donut-shaped heat/mass transfer element (e.g., an adsorbent processing medium) that rotates within a housing (e.g., a hermetic housing). As the heat/mass transfer element rotates, it sequentially exposes internal process fluid and heat transfer fluid flow passages within an associated processing medium (e.g., the adsorbent) to multiple manifolds. The multiple manifolds can (a) continuously supply a process fluid (e.g., methane gas mixture) to the processing medium which treats the process fluid (e.g., by removing impurities from the methane gas), and (b) continuously restore, replenish, regenerate or rejuvenate the processing medium before it processes additional fluid. This arrangement can be used to produce a continuous flow of processed fluid, with a reduced number of cyclic valves compared to similarly-functioning batch-mode purifying devices, or even zero valves (e.g., a valveless system), and other associated benefits that will be described in further detail below.

Figure 1:
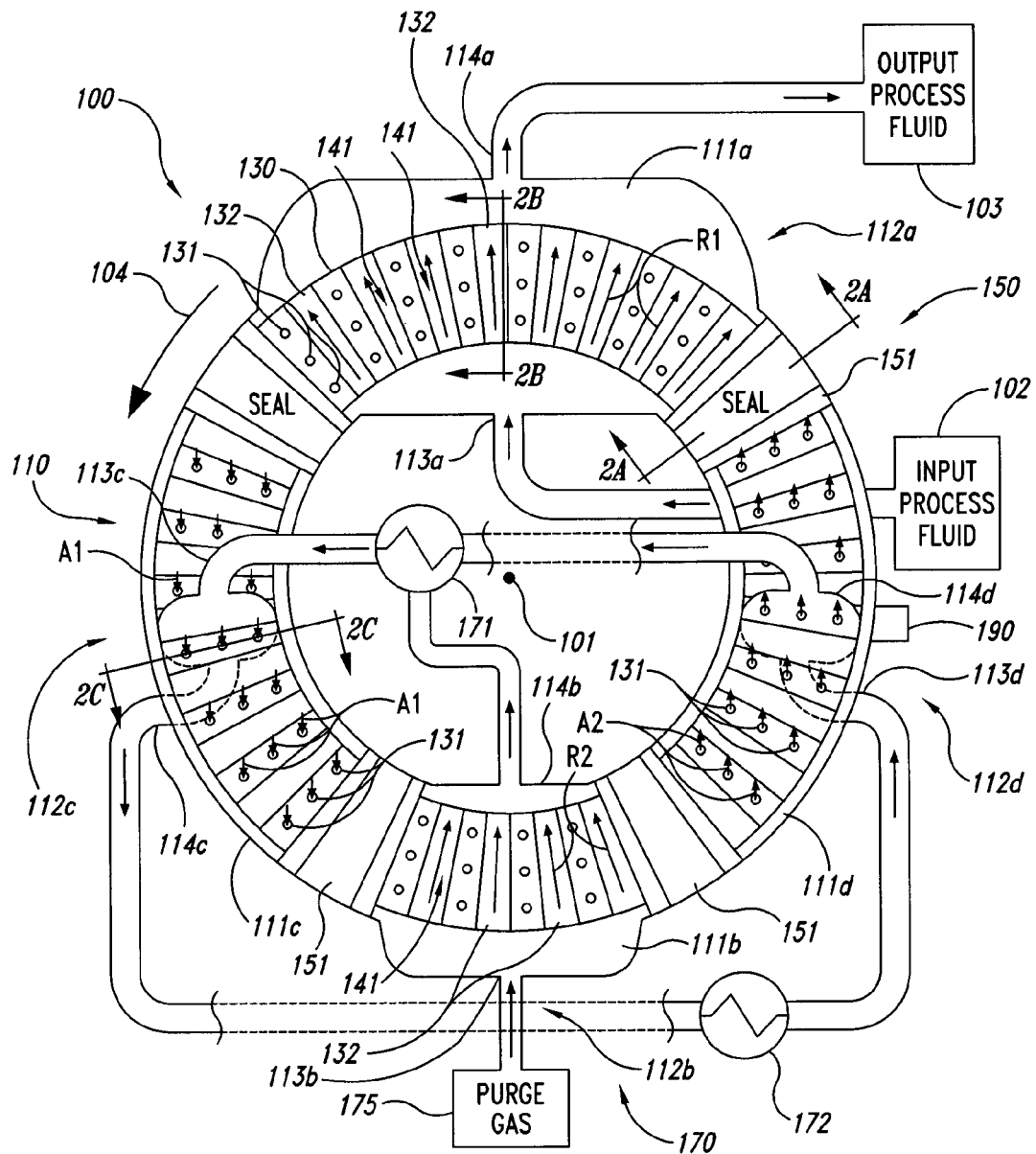
FIG. 1 is a partially schematic plan view of a rotary gas processing system having axial and radial flow paths configured in accordance with an embodiment of the disclosure.

FIG. 1 is a partially schematic, top plan view of a system 100 configured in accordance with an embodiment of the disclosure. The arrangement shown in FIG. 1 includes several simplifications to facilitate a clear disclosure of the technology. In at least some embodiments, suitable systems can be manufactured with these simplifications incorporated. In other embodiments, additional features (discussed later) are typically employed, e.g., to provide an overall system efficiency level suitable for commercial use. The system 100 can include a generally ring-shaped or toroidal heat/mass transfer element 130 positioned within a correspondingly shaped hermetic housing 110. The housing 110 can remain fixed, while the heat/mass transfer element 130 rotates within the housing about a rotation axis 101 that extends out of the plane of FIG. 1. Accordingly, the heat/mass transfer element 130 can be axisymmetric relative to the rotation axis 101. A driver 190 is operatively coupled to the heat/mass transfer element 130 to provide the continuous rotary motion. The housing 110 can include multiple manifolds 111 (four are shown in FIG. 1 as a first manifold 111a, a second manifold 111b opposite the first manifold 111a, a third manifold 111c between the first and second manifolds 111a, 111b, and a fourth manifold 111d opposite the third manifold 111c) positioned at corresponding regions 112 (four are shown as a first region 112a, a second region 112b opposite the first region, a third region 112c between the first and second regions 112a, 112b, and a fourth region 112d opposite the third region 112c). As the heat/mass transfer element 130 rotates about the rotation axis 101, as indicated by rotation direction arrow 104, each portion of the heat/mass transfer element 130 is sequentially exposed to each of the manifolds 111. The manifolds 111 collect and/or distribute fluid.

The heat/mass transfer element 130 includes both axial flow passages 131 and radial flow passages 132 that provide excellent thermal communication between the fluids they convey and an adsorbent processing medium 141, e.g., a adsorbent processing medium. However, the axial flow passages 131 are isolated from fluid communication with the radial flow passage 132. In the simplified schematic shown in FIG. 1, the intimate thermal communication between the fluids and the adsorbent processing medium 141 is somewhat obscured. Further details of representative embodiments that provide such thermal communication are described later with reference to FIGS. 11A-11G. At different manifolds, a flow of heat transfer fluid is permitted to pass through only the axial flow passages 131, or the process gas mixture is permitted to pass through only the radial flow passages 132, thus allowing effective contact between the adsorbent and different fluids in the two types of flow passages without mixing the flows in the two types of passages. Accordingly, a process fluid (e.g., an impure gas mixture) can be in intimate contact with the adsorbent processing medium 141 as it flows through the radial flow passages 132, and the adsorbent processing medium 141 can be regenerated by a hot or cold heat transfer fluid that flows through the axial flow passages 131. A seal arrangement 150 and relatively small pressure differences within the housing 110 prevent the different fluid streams from mixing within the housing around the heat/mass transfer element 130. Accordingly, the seal arrangement 150 can include full seals 151 between neighboring regions 112, and partial (e.g., axial flow only or radial flow only) seals within each region 112. Further details are described below at a general level with respect to FIGS. 2A-2C, and at a more detailed level with respect to FIGS. 3-12.

Continuing to refer to FIG. 1, the system 100 can be configured to perform a wide variety of processes on a wide variety of process gases or other fluids. Particular aspects of the system are described further below in the context of removing carbon dioxide and/or other impurities from a stream of methane gas. It will be understood by those of ordinary skill in the relevant art that similar systems and methods can be employed to perform other processes on other types of fluids. In general terms, particular embodiments of the disclosure are directed to performing an adsorption purification process on the process fluid at one or more regions (e.g., the first region 112a), and then regenerating/restoring the processing medium 141 at other regions (e.g., the second, third and fourth regions 112b, 112c, 112d).

In an embodiment shown in FIG. 1, an input process fluid 102 (e.g., a fluid having impurities) enters the first manifold 111a at a first entry port 113a. The input process fluid 102 passes radially outwardly through the heat/mass transfer element 130, as indicated by arrows R1. In the heat/mass transfer element 130, the input process fluid 102 can contact the processing medium 141 (e.g., an adsorbent) that removes certain impurities and thus purifies or otherwise treats the process fluid. For example, in a particular embodiment, the adsorbent can be configured to remove carbon dioxide, water, and/or hydrogen sulfide from a methane gas stream. The purified or otherwise processed fluid then exits the first manifold 111a through an exit port 114a, resulting in a flow of output process fluid 103.

As the heat/mass transfer element 130 rotates through the first manifold 111a, the processing medium 141 can become gradually saturated with impurities or depleted or otherwise experience a reduction in its ability to remove impurities. For example, an adsorbent processing medium 141 can become saturated with the impurities removed from the input process fluid 102. Accordingly, the processing medium 141 can be regenerated to remove the adsorbed impurities at the third region 112c. In a particular embodiment, the adsorbent processing medium 141 is regenerated by heating it to temperatures high enough to reduce the adsorptivity of impurities on the adsorbent to a negligible value thereby releasing the adsorbed impurities. Accordingly, the system 100 includes a heat transfer fluid flow path and heat exchanger arrangement 170 configured to heat the adsorbent processing medium 141 with a heat transfer fluid at the third region 112c. In a particular embodiment, the heat exchanger arrangement 170 can include a heater 171 that directs a heated heat transfer fluid (e.g., a regeneration gas) into the third manifold 111c through an entry port 113c, and then through the axial flow passages 131 of the heat/mass transfer element 130 in an axial direction (e.g., perpendicular to the plane of FIG. 1) as indicated by arrows A1. The hot heat transfer fluid exits the third manifold 111c at a corresponding exit port 114c at a lower temperature, as a result of transferring heat to the heat/mass transfer element 130. The heat received by the heat/mass transfer element 130 at the third region 112c releases the adsorbed impurities from the adsorbent processing medium 141.

As the heat/mass transfer element 130 continues to rotate, the adsorbent processing medium 141 is exposed to a hot purge gas at the second region 112b. In particular, hot purge gas from a hot purge fluid supply 175 passes into the second manifold 111b via an entry port 113b, and travels radially inwardly through the radial flow passages 132, as indicated by arrows R2. The purge fluid removes the impurities released from the adsorbent processing medium 141 in the third region 112c.

As the heat/mass transfer element 130 rotates further, the adsorbent processing medium 141 is exposed to the fourth manifold 111d at the fourth region 112d. In the fourth manifold 111d, the hot, clean heat/mass transfer element 130 is cooled, to prepare the adsorbent processing medium 141 to adsorb additional impurities by the time it rotates into the first manifold 111a. Accordingly, the heat exchanger arrangement 170 can include a cooler 172 that directs a cooled or cold heat transfer fluid into the fourth manifold 111d via an entry port 113d and through the axial flow passages 131 of the heat/mass transfer element 130, as indicated by arrows A2, to cool the heat/mass transfer element 130. The heat transfer fluid exits the third manifold 111c via a corresponding exit port 114d. As the heat/mass transfer element 130 continues to rotate, the cooled portion of the adsorbent processing medium 141 is again exposed to input process fluid 102 at the first region 112a. Accordingly, each portion of the adsorbent processing medium 141 is sequentially exposed to the process fluid, put into good thermal contact with a hot regeneration fluid, exposed to a hot purging fluid, and put into good thermal contact with a cold regeneration fluid.

In most cases, it is expected that the heat exchanger 170 will operate in a closed loop fashion (as discussed later with reference to FIG. 3) for increased thermal regeneration efficiency. In a simplified aspect of an embodiment shown in FIG. 1, the heat exchanger arrangement 170 operates in an open loop fashion. Accordingly, the heater 171 heats a regeneration fluid that passes through the second manifold 111b and is then disposed of. The cooling fluid separately passes through the fourth manifold 111d and is then also disposed of.

In a simplified closed-loop embodiment, illustrated in dashed lines in FIG. 1 the same fluid (e.g., a gas) used to heat and regenerate the adsorbent processing medium 141 is then cooled and used to cool and regenerate the adsorbent processing medium 141. In this embodiment, the fluid used in the closed loop heat exchanger can be compatible with or the same fluid as the primary component of the process fluid so that in the event some of the heat exchanger fluid remains in the heat/mass transfer element 130 after hot and cold regeneration, it does not interfere with the purification process conducted at the first region 112a or the purging process in the second region 112b. For example, the heat transfer fluid can include pure methane gas when the input process fluid 102 includes methane gas containing impurities. A more complex closed-loop arrangement is described later with reference to FIG. 3.

Figure 2A:
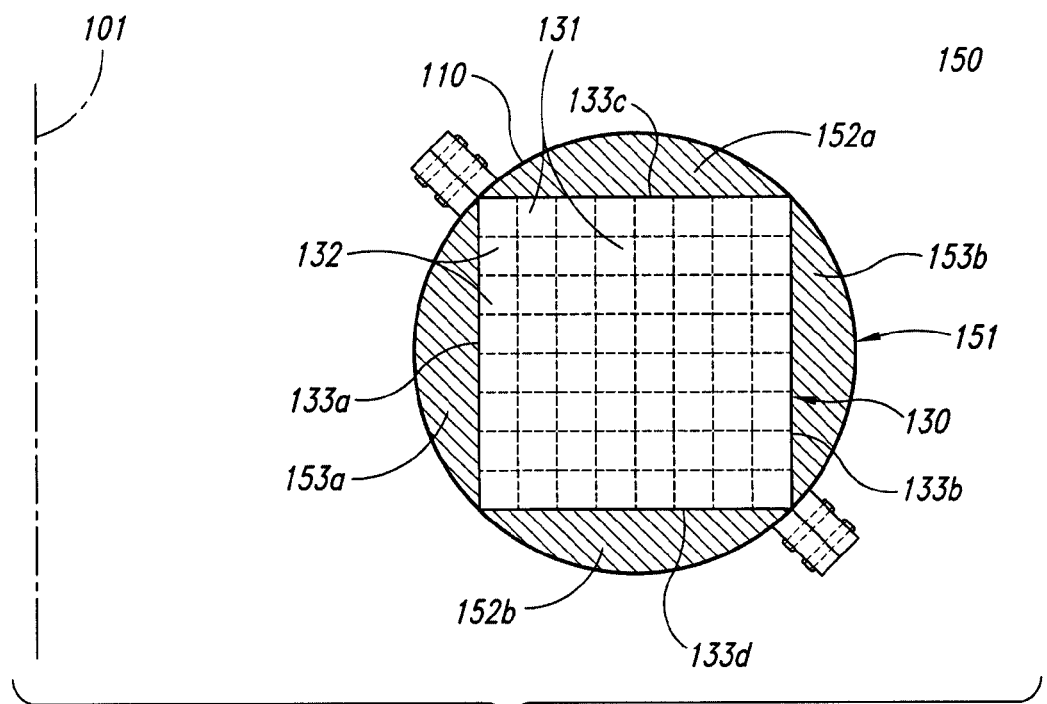
FIG. 2A is a partially schematic illustration of a system seal positioned to seal axial and radial flow paths in accordance with an embodiment of the disclosure, taken substantially along line 2A-2A of FIG. 1.
Figure 2B:
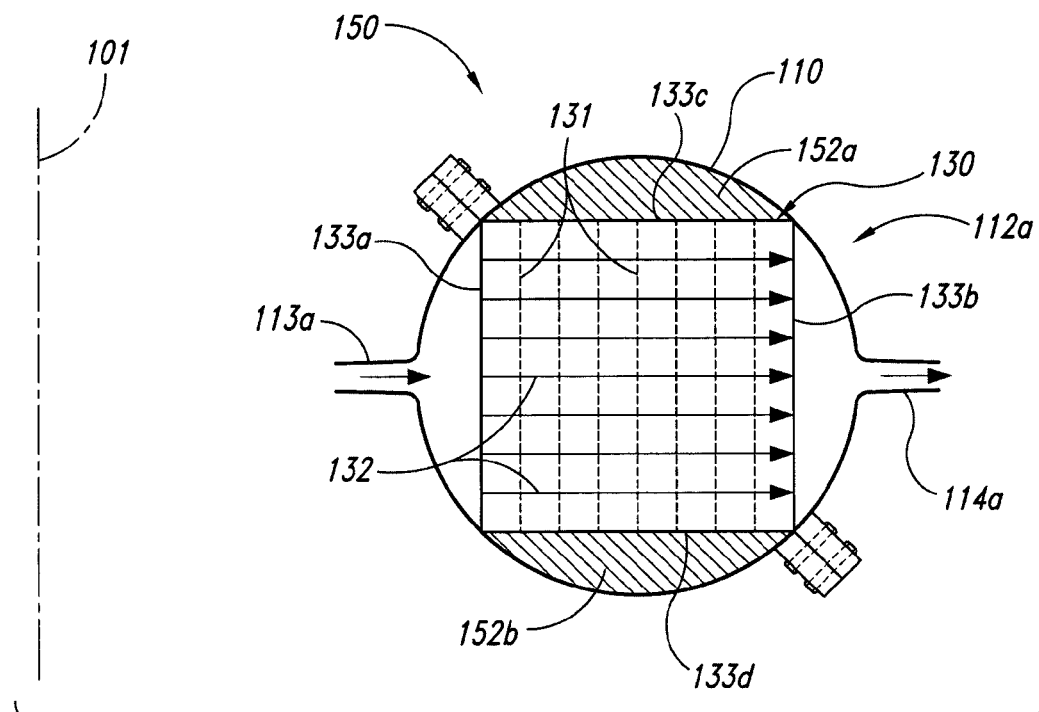
FIG. 2B is a partially schematic, cross-sectional illustration of a system seal positioned to seal axial flow paths in accordance with an embodiment of the disclosure, taken substantially along line 2B-2B of FIG. 1.
Figure 2C:
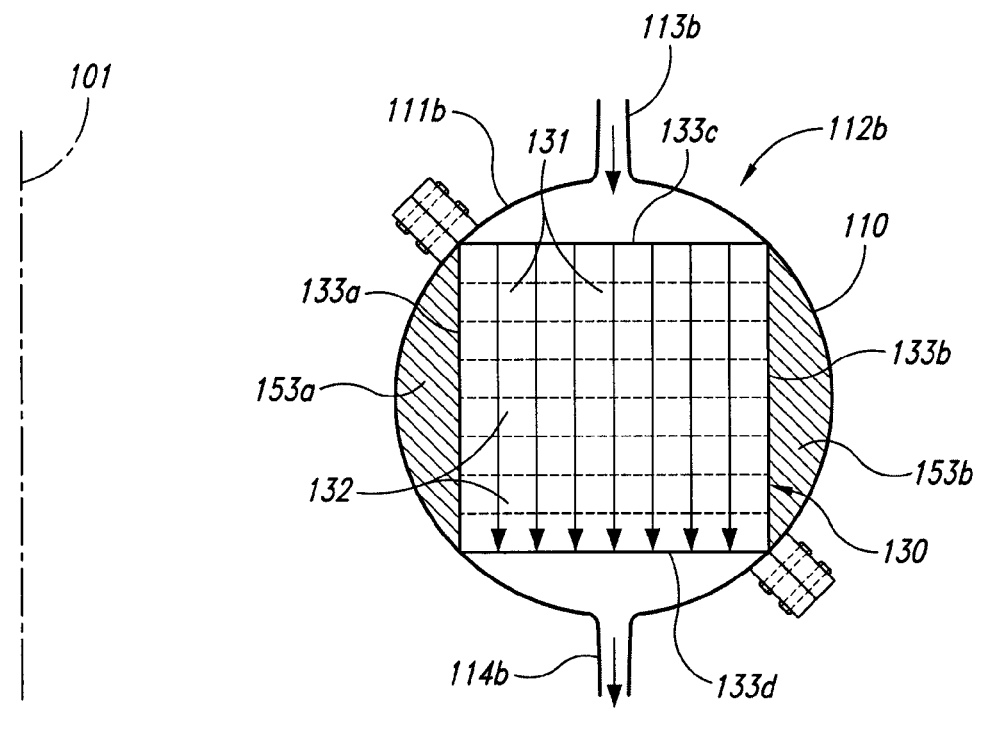
FIG. 2C is a partially schematic, cross-sectional illustration of a system seal positioned to seal radial flow paths in accordance with an embodiment of the disclosure, taken substantially along line 2C-2C of FIG. 1.

FIGS. 2A-2C are cross-sectional illustrations of the heat/mass transfer element 130, the housing 110, and associated seals 150 employed at various points around the circumference of the housing 110 shown in FIG. 1. For example, FIG. 2A is a representative cross-sectional illustration of the housing 110 and the heat/mass transfer element 130 at one of the full seals 151 shown in FIG. 1. As shown in FIG. 2A, the heat/mass transfer element 130 includes radial process fluid flow paths or passages 132 that extend transverse to the rotation axis 101, and axial heat transfer fluid flow paths or passages 131 that extend generally parallel to the rotation axis 101. The radial flow passages 132 are positioned to allow contact (e.g., direct contact) between the adsorbent material and the process fluid, and the axial flow passages 131 are positioned in excellent thermal communication with the adsorbent material 141 described above, but are isolated from direct fluid communication with the process fluid in the heat/mass transfer element 130.

In a particular embodiment, both the hermetic housing 110 and the heat/mass transfer element 130 have generally toroidal shapes, but the inner surface of the housing 110 is circular while the outer surface of the heat/mass transfer element 130 is rectangular or, in particular embodiments, square. Accordingly, the seal arrangement 150 includes seals that are shaped to fit within the gap between these surfaces, while allowing the heat/mass transfer element 130 to rotate relative to the housing 110, and while preventing or at least significantly restricting circumferential flow between the axial flow passages 131 on the one hand and the radial flow passages 132 on the other. At the full seal 151, which is located between adjacent regions 112 (FIG. 1) of the system 100, no flow passes in either the axial direction or the radial direction. Accordingly, both the axial flow passages 131 and the radial flow passages 132 are shown in phantom lines in FIG. 2A. The full seal 151 can include an inner radial seal 153a that seals against a first ring-shaped side 133a of the heat/mass transfer element 130, and an outer radial seal 153b that seals against a corresponding second ring-shaped side 133b of the heat/mass transfer element 130. The full seal 151 can further include an upper axial seal 152a that seals against a third ring-shaped side 133c of the heat/mass transfer element 130, and a lower axial seal 152b that seals against a fourth ring-shaped side 133d of the heat/mass transfer element 130.

FIG. 2B illustrates a portion of the seal arrangement 150 at the first region 112a and the second region 112b. In the first region, the cool process fluid flows through the radial flow passages 132 (shown in solid lines) from the entry port 113a to the exit port 114a. Accordingly, the first and second sides 133a, 133b of the heat/mass transfer element 130 are exposed to the entry and exit ports 113a, 114a, while the upper axial seal 152a and the lower axial seal 152b seal the axial flow passages 131 (shown in phantom lines). As a result, the process fluid passes through the heat/mass transfer element 130 without entering the axial flow passages 131.

FIG. 2C illustrates the heat/mass transfer element 130 at the third region 112c. In this region, the axial flow passages 131 are opened and the radial flow passages 132 are sealed. Accordingly, the inner radial seal 153a and the outer radial seal 153b seal the radial flow passages 132 from communication with the second manifold 111b. The third and fourth sides 133c, 133d of the heat/mass transfer element 130 are exposed to the entry port 113b and exit port 114b to allow the regenerative heat transfer fluid to pass from the entry port 113b to the exit port 114b. A generally similar arrangement is used at the fourth region 112d and fourth manifold 111d (FIG. 1).

Figure 3:
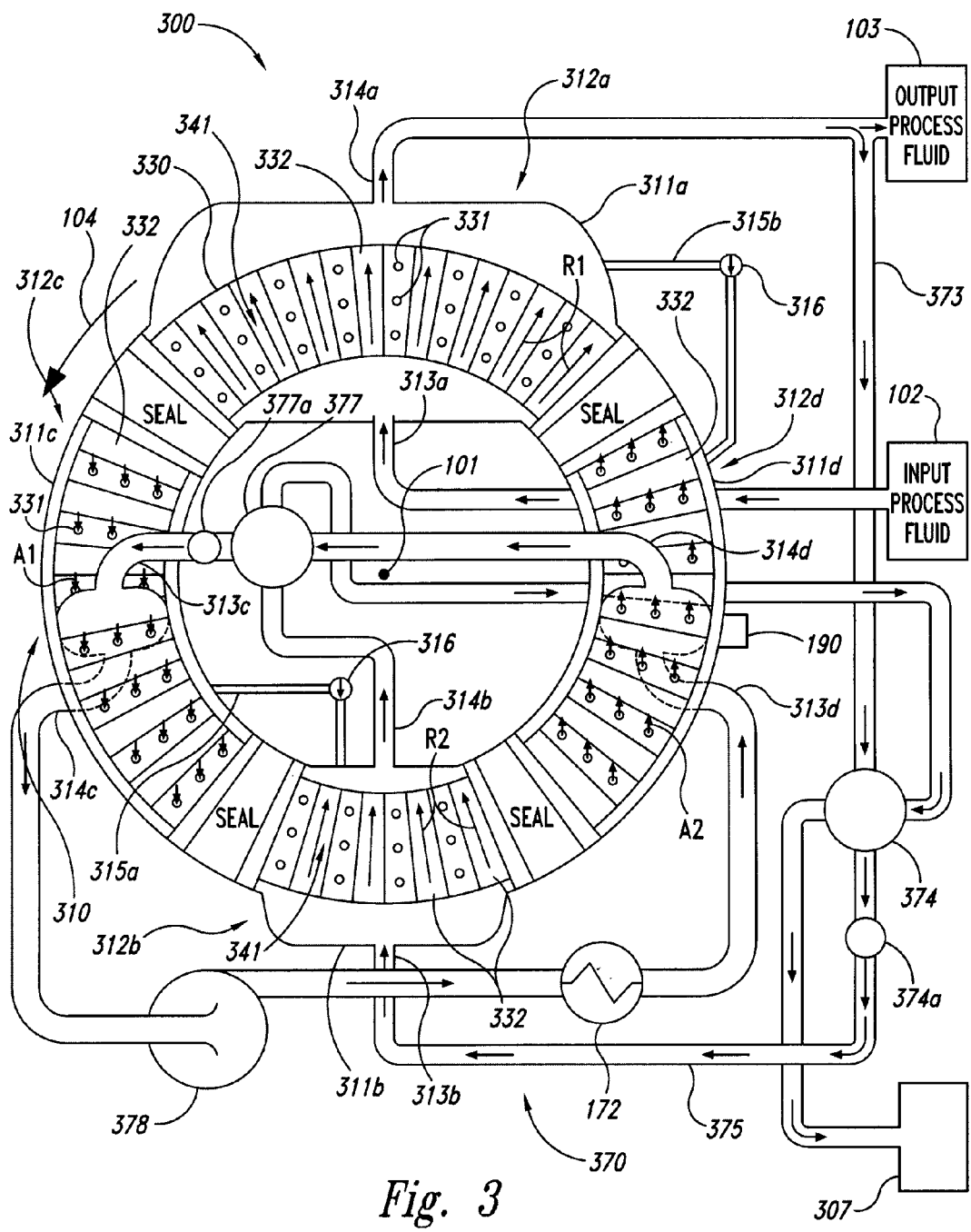
FIG. 3 is a partially schematic plan view of a rotary gas processing system having four regions configured in accordance with another embodiment of the disclosure.

FIG. 3 is a more detailed, top plan schematic view of a system 300 configured in accordance with another embodiment of the disclosure. The system 300 has the same general arrangement described above with reference to FIG. 1 as well as several additional features. These additional features include (a) an arrangement of pressure equalization paths around the housing that allow different regions of the overall system 300 to operate at the same internal pressure despite large thermal transitions, and (b) additional closed loop heat exchanger arrangements that enhance the overall efficiency of the system. These aspects may be included all together on the same system as shown in FIG. 3, or these features may be selected individually or in other combinations in other embodiments.

The system 300 includes a heat/mass transfer element 330 and associated processing medium 341 that rotate within a housing 310 having four manifolds 311a-311d positioned at four corresponding circumferential regions 312a-312d. Each manifold 311a-311d has a corresponding entry port 313a-313d and exit port 314a-314d. At the first manifold 311a, the input process fluid 102 is directed through the adsorbent processing medium 341 to produce an output process fluid 103 in a manner generally similar to that described above. At the third manifold 311c, the adsorbent processing medium 341 is regenerated via heating, and at the fourth manifold 311d, the adsorbent processing medium 341 is cooled, both in a manner generally similar to that described above. A heat exchanger arrangement 370 shown in FIG. 3 is configured in a closed loop so that the same heat transfer fluid used to heat the adsorbent processing medium 341 at the third region 312c is used to cool the adsorbent processing medium 341 at the fourth region 312d. A pump or blower 378 circulates the heat transfer fluid around the heat exchanger loop, through the cooler 172 (e.g., a trim cooler) and a trim heater 377a. The heater 171 described above with reference to FIG. 1 has been combined with a regeneration fluid heat exchanger 377 that receives waste heat from a purge process fluid and a trim heater, described further below.

The second manifold 311b is positioned opposite the first manifold 311a, between the third manifold 311c and the fourth manifold 311d to purge desorbed contaminants from the heat/mass transfer element 330. Accordingly, the second manifold 311b receives clean hot purge fluid (e.g., clean methane) from a heated purge fluid supply 375 and directs the hot purge fluid through the radial flow passages 332, as indicated by arrows R2. As the clean hot purge fluid passes through the radial flow passages 332 of the heat/mass transfer element 330, it carries out desorbed contaminants (e.g., carbon dioxide) from the adsorbent processing medium 341. Because the heat/mass transfer element 330 and adsorbent processing medium 341 have been heated (e.g., to about 500° F.) at the third region 312c, the purge fluid is heated to the same hot temperature before passing through the adsorbent processing medium 341 in the second region 312b. The hot purge fluid can accordingly be used to preheat the heat transfer fluid at the regeneration fluid heat exchanger 377 and trim heater 377a before the heat transfer fluid enters the third region 312c. The used and still hot purge fluid can also pass through a purge fluid heat exchanger 374 where it preheats the clean incoming purge fluid before the incoming purge fluid enters the second manifold 311b. After passing through the purge fluid heat exchanger 374, the cooled used purge fluid can be used as fuel for a power generator for the system or otherwise beneficially disposed of. In a particular embodiment, the purge fluid is received from a purge fluid supply 373 that is drawn off the output process fluid 103. Accordingly, the purge fluid can include purified methane. After passing through the purge fluid heat exchanger 374, the purge fluid can pass through a trim heater 374a to reach a suitably high temperature before entering the second region 312b. Even after mixing with the desorbed contaminants at the second region 312b, the used purge fluid can still be burned to produce power, for example, at a genset 307 or other device.

One feature of the arrangement shown in FIG. 3 is that the heat/mass transfer element 330 and the associated adsorbent processing medium 341 undergo significant thermal changes as the heat/mass transfer element 330 rotates through a complete cycle. For example, the temperature of the adsorbent processing medium 341 at the third region 312c can reach about approximately 500° F. during a representative desorption process. As a result, the desorbed impurities will incrementally begin to increase the pressure in the hot processing medium segments containing the adsorbent. However, the radial flow passages 332 are generally sealed in the third region 312c (e.g., as shown in FIG. 2C) so that the pressure in the processing medium segment could increase by the ratio of the average absolute temperatures in region 312a and 312c. Accordingly, to avoid such a pressure increase the system 300 can include features to reduce or prevent pressure differences that could cause leakage of fluids between different regions through the seals. These features can include multiple pressure equalization paths 315, e.g., a first pressure equalization path 315a that couples the adsorbent and radial flow passages 332 at the third region 312c with the exit port 314b at the second region 312b. Accordingly, desorbed fluids and residual process fluid within the radial flow passages 332 at the third region 312c can mix with the desorbed fluids purged at the second region 312b, and exit the system 100, while at the same time reducing or eliminating pressure differences that may build up in the third region 312c as a result of heating for regeneration. In a particular embodiment, the first pressure equalization path 315a can include a one-way valve 316 that prevents purged contaminants from reentering the heat transfer element 330. The first pressure equalization path 315a can accordingly equalize the pressure between the third region 312c and the second region 312b without contaminating the heat/mass transfer element 330.

The system 300 can include other pressure equalization paths that operate in a generally similar manner to equalize pressures at other points around the circumference of the housing 310. For example, the heat/mass transfer element 330 will cool and the pressure of the residual gas in the adsorbent and radial flow segments 332 will decrease at the fourth region 312d. To reduce or prevent pressure differences between the wheel segments of the heat/mass transfer element 330, the system 300 can include a second pressure equalization path 315b and one-way valve 316 connected between the exit port 314a of the first manifold 311a, and the radial flow passages 332 within the fourth manifold 311d. This arrangement will allow an adequate amount of purified process fluid to enter the adsorbent in the radial flow passages 332 at the fourth manifold 311d, thus continuously equalizing the pressure between these two regions during cooling in the regeneration.

An advantage of the foregoing arrangement is that the entire system 300 can be operated at a single generally uniform internal pressure. For example, the internal pressure of the hermetic housing 310 can have a value of from about 80 psia to about 150 psia, and in a particular embodiment about 120 psia. In other embodiments, the internal pressure can be higher than 150 psia (e.g., 300-350 psia) provided the housing 310 and associated fluid paths and systems are designed to withstand such loads. By equalizing the internal pressure among the regions 312a-312d, the structural stresses on the system components and in particular, the demands placed on the seals, can be reduced or eliminated. Accordingly, it is expected that this arrangement will be more cost effective over the life of the system 300.

Another advantage of the foregoing arrangement is that the system 300 can operate in a continuous flow manner. In particular, input process fluid can be continuously supplied to the system 300 as the heat/mass transfer element 330 rotates, and the heat exchanger arrangement 370 can continuously operate to thermally regenerate the adsorbent processing medium 341. To facilitate a continuous operation, the sizes of the processing regions 312a-312d can be determined in a manner that enhances (e.g., optimizes) the overall efficiency of the system 300. For example, the adsorbent processing medium 341 may require less time to undergo the purge operation in the second region 312b than it requires to perform the contaminant removal adsorption process in the first region 312a. Accordingly, because the heat/mass transfer element 330 is expected to rotate continuously at a constant rate, the circumferential extent of the second region 312b can be less than the circumferential extent of the first region 312a, and is typically the smallest of the four regions. The adsorbent processing medium 341 may require more time at the third region 312c for heating and desorption, than at the fourth region 312d for cooling. Depending on factors that include specific flow rates and heat transfer coefficients, the circumferential extents of the third region 312c and the fourth region 312d can be greater or lesser than that of the first region 312a.

FIGS. 4-11F illustrate particular features associated with particular embodiments of the system 300 to carry out the processes described above. Beginning with FIG. 4, the system 300 includes a donut-shaped hermetic housing 310 that includes an upper housing portion 317a and a lower housing portion 317b. Each of the housing portions 317a, 317b includes a flange 319 that extends outwardly and is used to removably connect (e.g., bolt) the two housing portions together with a hermetic sealant circumferentially inside the flange bolt circle. The housing 310 encloses the four processing regions 312a-312d, which are generally bounded (e.g., welded) as indicated by dashed lines in FIG. 4. A selected number of entry and exit ports are visible in FIG. 4, including the first exit port 314a at the first region 312a, the second entry port 313b at the second region 312b, the third entry port 313c at the third region 312c, and the fourth exit port 314d at the fourth region 312d. Hermetic bearing ports 318 allow access to circumferentially positioned bearings, which are described in greater detail later with reference to FIG. 8. The bearings allow the heat/mass transfer element 330 (not visible in FIG. 4) to rotate smoothly within the housing 310. Power is provided to the heat/mass transfer element 330 via a driver 190 contained in a driver housing 191.

Figure 4:
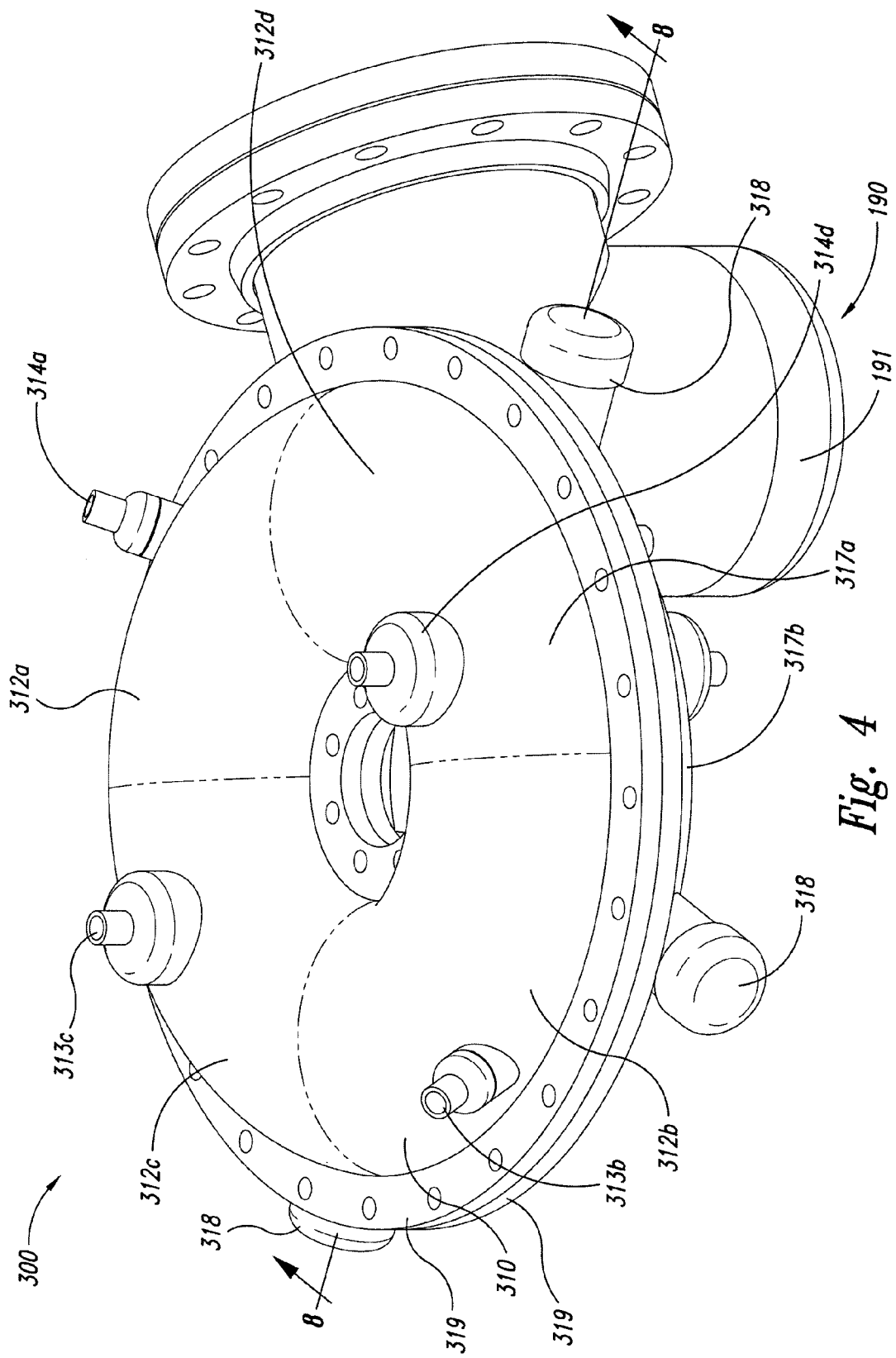
FIG. 4 is a partially schematic, isometric view of an embodiment of the system shown in FIG. 3.
Figure 5:
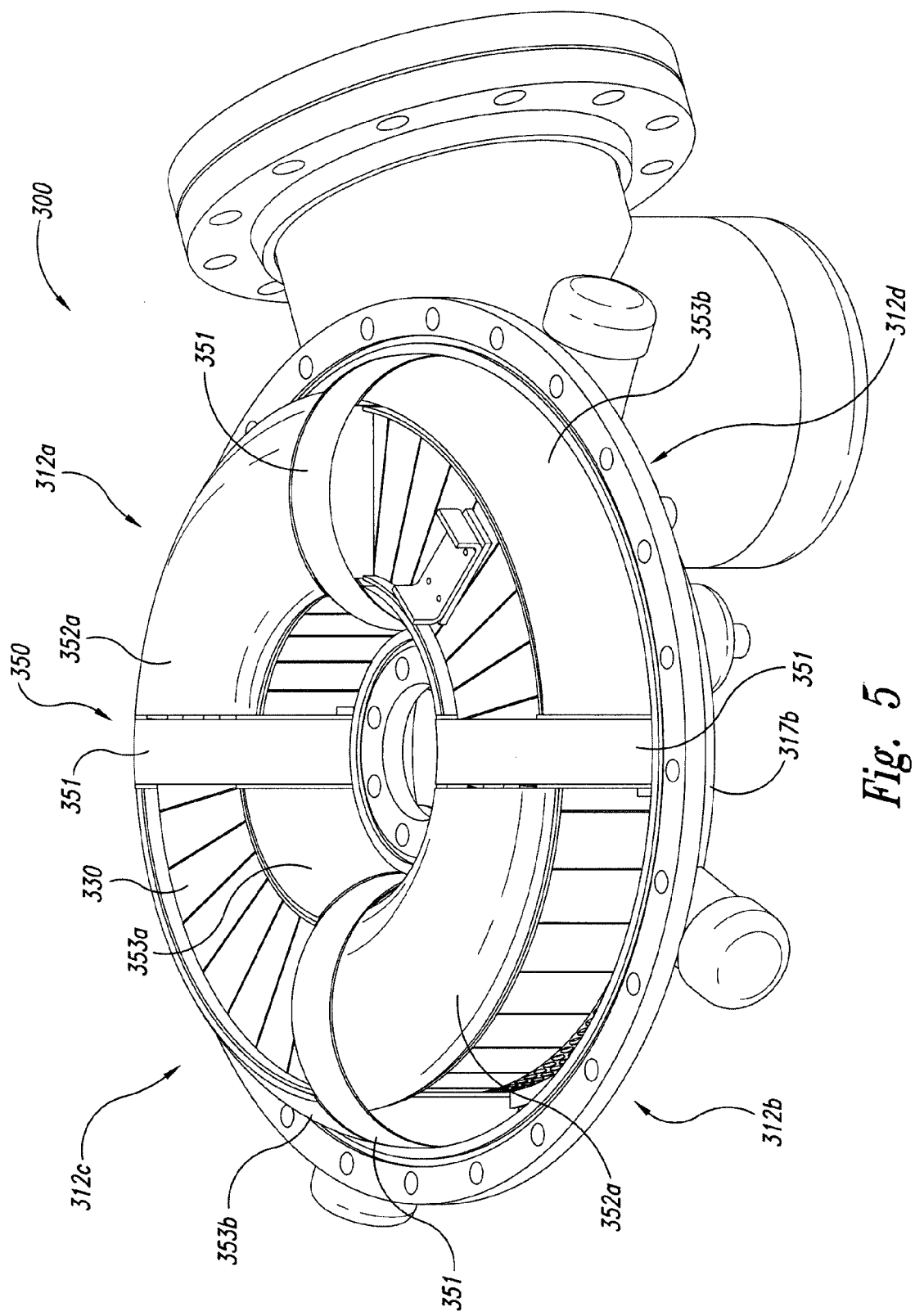
FIG. 5 is a partially schematic, isometric view of an embodiment of the system shown in FIG. 4, with an upper housing portion removed.

FIG. 5 illustrates an embodiment of the system 300 shown in FIG. 4, with the upper housing portion 317a removed. Accordingly, the heat/mass transfer element 330 and the seal arrangement 350 are visible in FIG. 5. The seal arrangement 350 includes four full seals 351 that prevent flow in both the radial and axial directions through the heat/mass transfer element 330. The seal arrangement 350 also includes the axial and radial seals described above. Several of the seals are visible in FIG. 5, including the upper axial seals 352a at the first and second regions 312a, 312b, and the inner and outer radial seals 353a, 353b at the third and fourth regions 312c, 312d.

Figure 6:
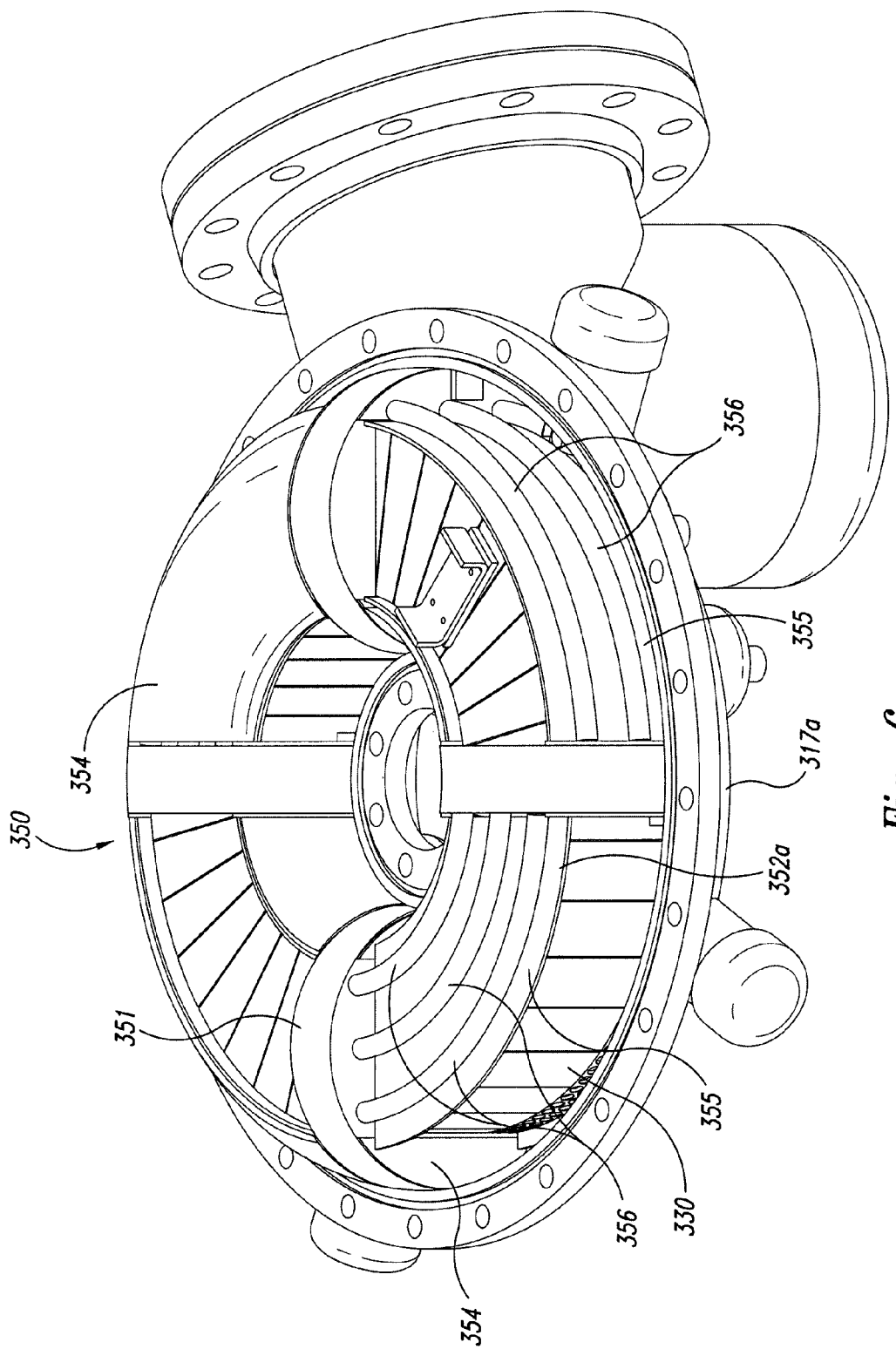
FIG. 6 is a partially schematic, isometric view of the system shown in FIG. 5 with selected seal portions removed.

FIG. 6 illustrates the seal arrangement 350 with portions removed to expose features below. In particular, the radial and axial seals can include a volume of high-temperature foam 354 that is positioned over multiple circumferentially extending tubes 356. The tubes 356 are positioned against a seal sheet 355. When the high temperature foam 354 is compressed between the first housing portion 317a (FIG. 4) and the second housing portion 317b, it presses against the tubes 356, which in turn locally press on the seal sheet 355 to form a labyrinth seal with the heat/mass transfer element 330 just below. In a particular embodiment, the tubes 356 can be hollow. In further particular embodiments, the tubes 356 can include a fluid that is selectively pressurized to vary the local force provided by the tubes 356 against the seal sheet 355. The seal sheet 355 can include Rulon® or another suitable durable low-friction material.

Figure 7:
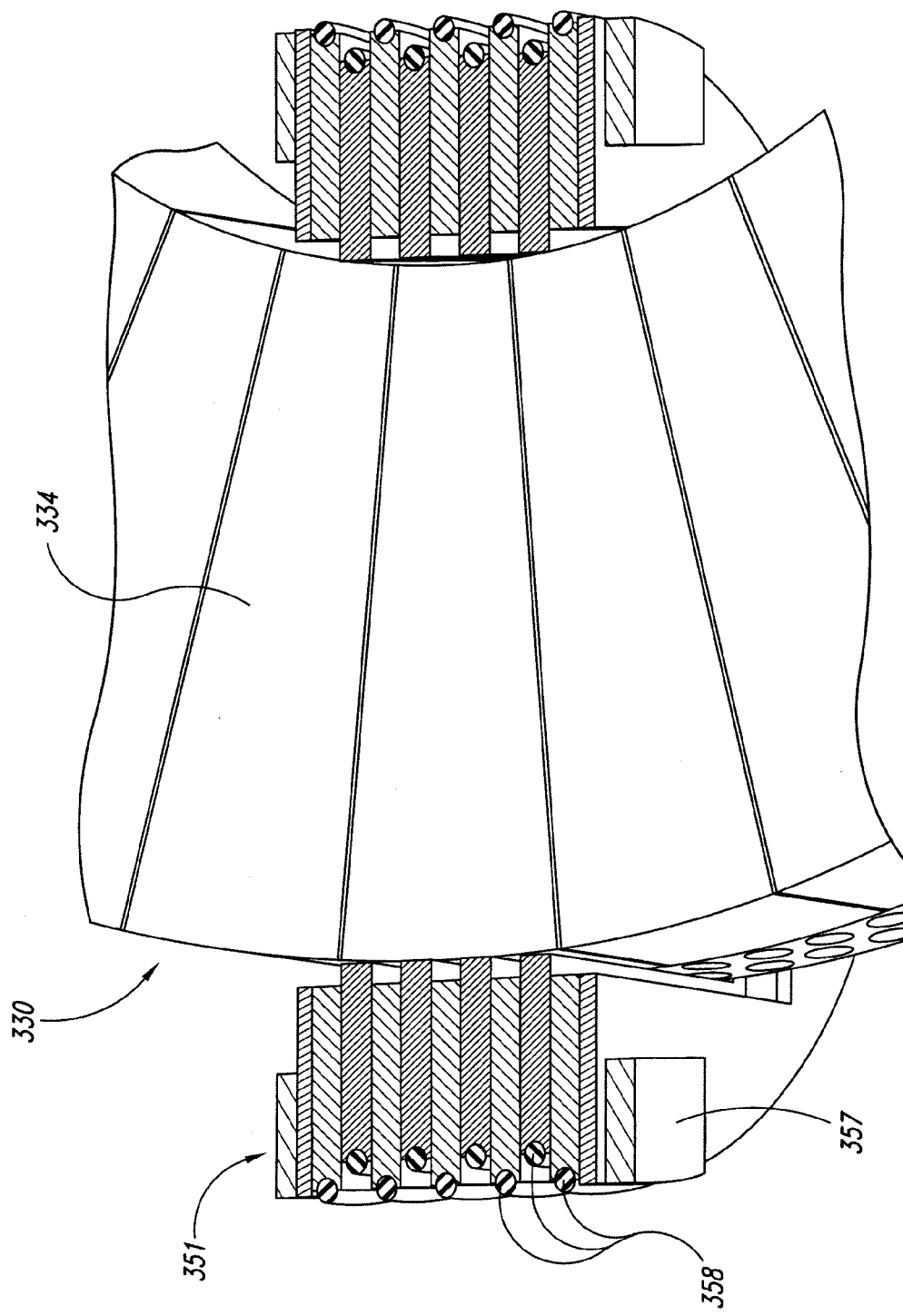
FIG. 7 is a partially schematic, cut-away view of a system seal configured in accordance with an embodiment of the disclosure.

FIG. 7 is a detailed, partially cut-away illustration of one of the full seals 351 described above. The full seals 351 can extend entirely around the heat/mass transfer element 330 and can include a pair of seal supports 357 positioned on opposite sides of a series of seal elements 358. The seal elements 358 can form a labyrinth seal around all sides of the heat/mass transfer element 330. The heat/mass transfer element 330 can include generally pie-shaped segments 334 that contain the axial and radial flow passages and the adsorbent processing medium, as will be described in further detail later with reference to FIGS. 11A-11G.

Figure 8:
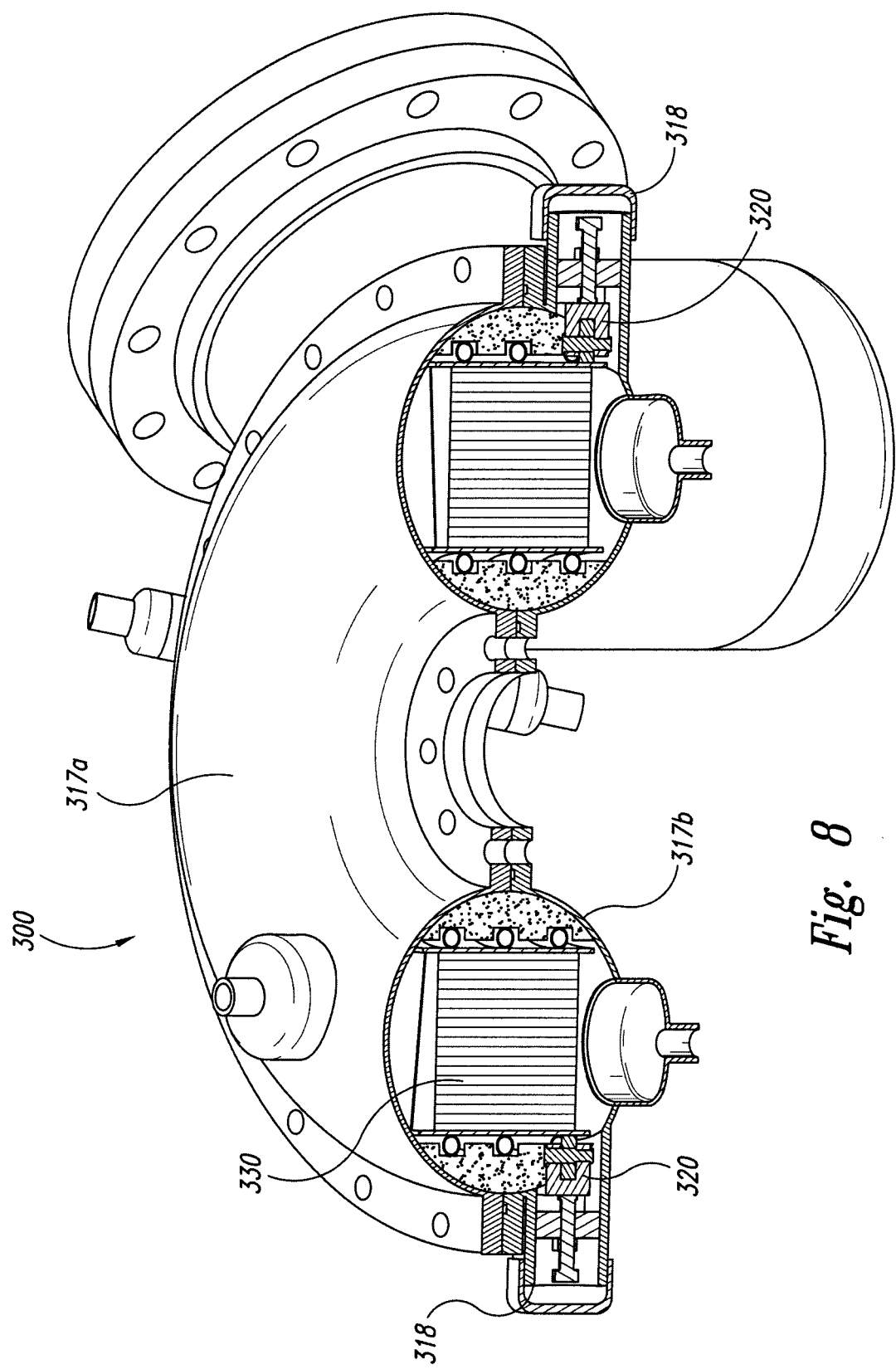
FIG. 8 is a partially schematic, cross-sectional view of an embodiment of the system shown in FIG. 4.

FIG. 8 is a partially schematic, cut-away view of the system 300 taken generally along line 8-8 of FIG. 4. FIG. 8 illustrates the structure located inside the bearing ports 318, including bearings 320 that engage the outer peripheral surface of the heat/mass transfer element 330. The bearing port 318 allows a manufacturer or user to adjust the bearing 320 to appropriately guide the heat/mass transfer element 330 as it rotates within the housing 310.

Figure 9:
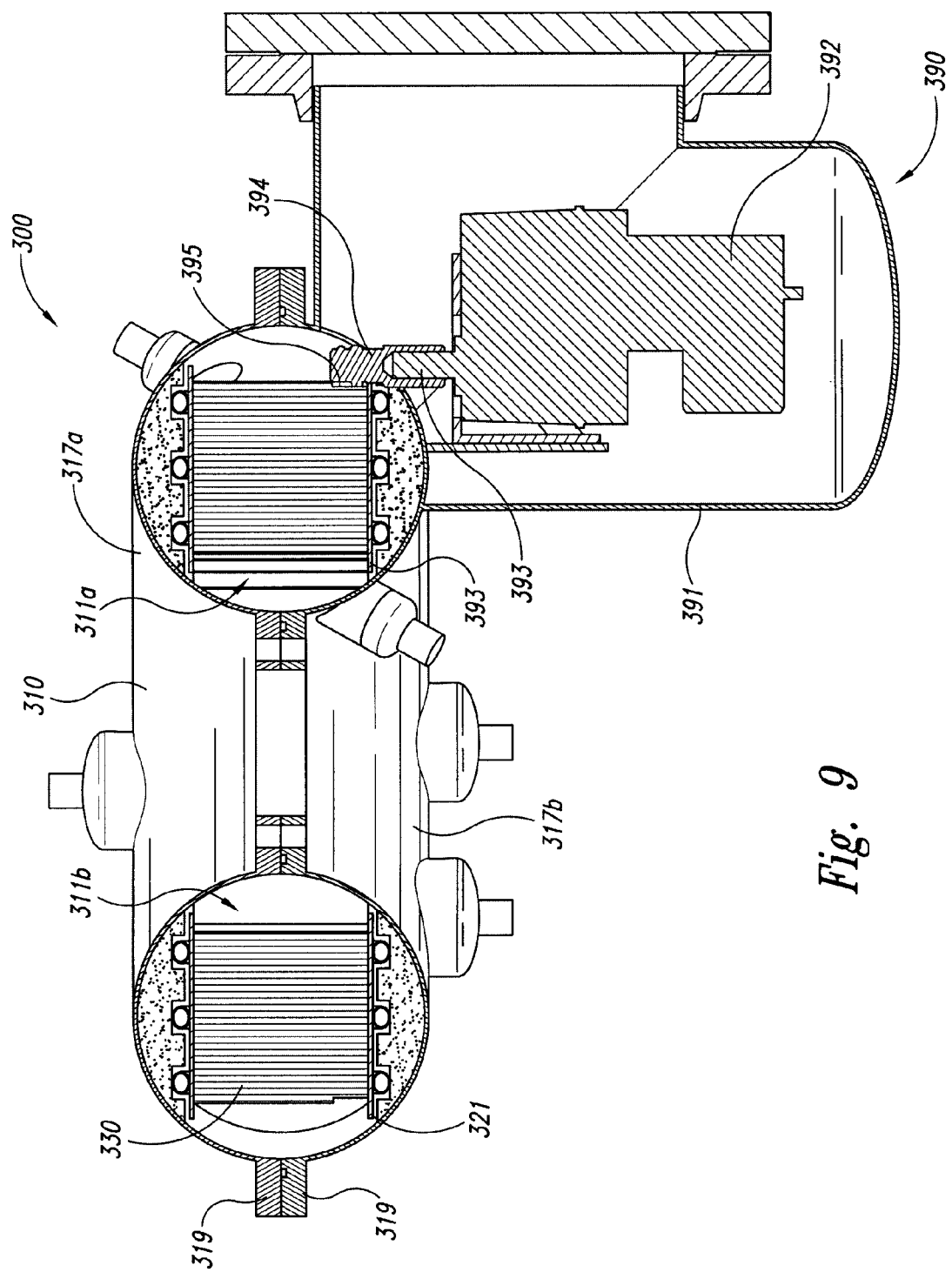
FIG. 9 is another partially schematic, cross-sectional view of an embodiment of the system shown in FIG. 4, illustrating a representative driver arrangement.

FIG. 9 is a partially schematic, cut-away illustration of the system 300 illustrating further details of the driver 390. The driver 390 is positioned within the driver housing 391 and can include a motor 392 or other motive element coupled to a shaft 393 that extends upwardly into the housing 310. The shaft 393 can include a pinion 394 that meshes with a corresponding rack 395 carried by the heat/mass transfer element 330. In other embodiments, the driver 390 can be operatively coupled to the heat/mass transfer element 300 with other suitable arrangements, e.g., a belt or chain drive. The heat/mass transfer element 330 can be supported in the housing 310 via the bearings 320 described above with reference to FIG. 8, and via low-friction axial supports 321. The driver 390 can include an appropriate gear reduction arrangement to rotate the heat/mass transfer element at an appropriate rate. In a particular example, the heat/mass transfer element 330 rotates at about one revolution per hour. The rate selected for rotating the heat/mass transfer element 330 can depend upon a variety of design factors, including the overall size of the system 300 and the flow rates of fluids through the system.

Figure 10A:
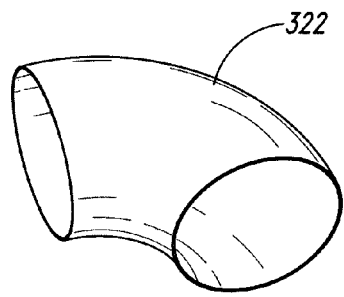
FIGS. 10A-10C illustrate a method for manufacturing a housing in accordance with an embodiment of the disclosure.
Figure 10B:
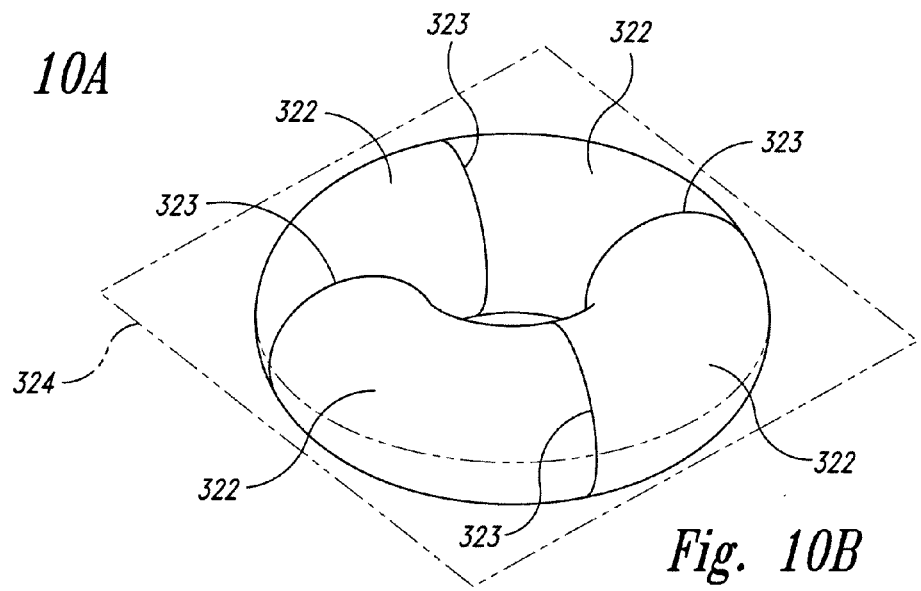
Figure 10C:
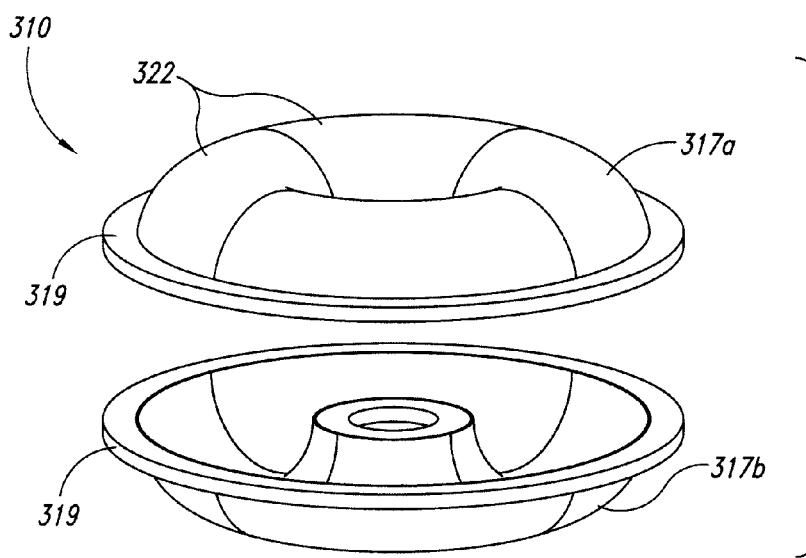

As described above, the housing 310 can have a ring shape and in particular embodiments, a toroidal or donut shape. The housing 310 can be manufactured using a variety of techniques, a representative one of which is shown in FIGS. 10A-10C. In this embodiment, the housing is assembled using multiple pre-formed pipe sections, as shown in FIG. 10A. The pipe sections can include multiple elbow sections 322 that each extend circumferentially around a fraction of a circle. As shown in FIG. 10B, four such elbow sections 322, each extending circumferentially through a 90° arc can be connected to each other using welds 323, forming a closed, annular, ring-shaped conduit. The assembled sections 322 can then be cut at a parting plane 324 to form the upper housing portion 317a and the lower housing portion 317b, shown in FIG. 10C. The manufacturer can then add a flange 319 to each of the two housing portions 317a, 317b to allow the housing portions to be releasably attached to each other with appropriate sealing material between the flanges on the housing and around the heat/mass transfer element 330 (FIG. 9). It is expected that this manufacturing technique can be significantly less expensive than others, including techniques that require the entire housing 310 to be formed from a single piece of stock. It is also expected that the circular cross-sectional shape of the housing 310 can efficiently hermetically contain the internal pressure loading without significantly bowing or otherwise potentially compromising the integrity of the seal arrangement and/or the rotation of the heat/mass transfer element. However, in at least some embodiments, the housing 310 may have a different cross-sectional shape, e.g., a square or rectangular cross-sectional shape e.g., for applications with relatively low internal pressure differentials between the region inside the housing and the region outside the housing such that little or no distortion of the housing occurs and it remains close fitting to the heat/mass transfer element.

FIGS. 11A-11G illustrate representative techniques for positioning an adsorbent processing medium 341 in the segments 334 of the heat/mass transfer element 330 described above with reference to FIG. 7. In general, the adsorbent processing medium 341 is in direct fluid contact with a fluid (e.g., an impure process mixture) passing through one of (a) the axial passages or (b) the radial passages, and is in good thermal communication (but not direct fluid communication) with heat transfer fluid passing through the other of (a) the axial passages or (b) the radial passages.

Beginning with FIG. 11A, a representative segment 334a can include axial tubes 335 having outer surfaces with an adsorbent processing medium coating 336. The adsorbent processing medium 341 can include any appropriate absorbent that selectively removes certain impurities from process gas streams in particular embodiments, e.g., zeolites or activated alumina or activated carbon material in further particular embodiments. The axial tubes 335 are packed close together so as to be in line-to-line or point-to-point contact with each other. A process fluid flow 305 passes through the adsorbent processing medium 341 in a radial direction R. The hot or cold regenerating fluid (e.g., heat transfer fluid) can then pass through the axial tubes 335 in an axial direction (e.g., perpendicular to the plane of FIG. 11A) to heat or cool the adsorbent processing medium 341. The impurities are removed by a purge gas flow in direct contact with the hot adsorbent in the radial direction R.

FIG. 11B illustrates a representative segment 334b having another arrangement in which the axial tubes 335 are packed with small adsorbent processing medium beads 337. In this embodiment the process fluid flows axially through the tubes 335 to contact the adsorbent processing medium 341 inside, and the hot or cold regenerating fluid flows radially among the tubes as indicated by arrow R. The purge fluid also flows axially through the tubes 335 to remove the desorbed impurities.

In FIG. 11C, a generally standard arrangement of a cross-flow heat exchanger grid material is positioned within a representative segment 334c. Either the axial or the radial flow passages are then packed with the adsorbent processing medium. An advantage of this arrangement is that it is relatively simple to obtain a suitable cross-flow heat exchanger grid material and cut it to a rectangular size that fits within the segment 334c. However, this arrangement creates dead spaces 340 in which the heat exchanger grid cannot be positioned without blocking the radial flow passages near the circumferential boundaries of the segment 334. Accordingly, an advantage of the arrangements described above with reference to FIGS. 11A and 11B is that they do not include a dead space 340. Put another way, a standard rectangular cross-flow heat exchanger grid does not readily fit in the tapered annular space of the segments 334, while the axially extending tubes shown in FIGS. 11A and 11B do.

FIG. 11D illustrates a segment 334d having axially extending tubes 335 that carry a hot or cold regeneration fluid, and extend through axially layered highly thermally conducting screens 338. The screens 338 include a fine mesh having mesh openings that can each support an individual adsorbent processing medium bead 337. Accordingly, the process fluid flow 305 is directed radially over and around the adsorbent beads 337, while the regeneration fluid flow is directed axially through the axial tubes 335 such that the screen efficiently indirectly heats or cools the adsorbent beads as they rotate through the regenerative sections of the temperature swing adsorption cycle. FIG. 11E is a cross-sectional view of one of the tubes 335 shown in FIG. 11D and further illustrates the location of the adsorbent processing medium beads 337 between layers of screen 338.

FIG. 11F illustrates a segment 334f that includes multiple tapered tubes 339 extending radially outwardly. Each of the tapered tubes 339 can include an arrangement of adsorbent processing medium beads 337 that are also arranged in a radially outward direction. The adsorbent processing medium beads 337 can have different diameters to take advantage of the increasing width (in a radially outward direction) of the tapered tubes 339. Accordingly, smaller beads 337 can be positioned radially inwardly in each tube 339, and larger beads 337 can be positioned radially outwardly. Process fluid 305 flows radially outwardly (or inwardly), and regeneration fluid flows axially in spaces between neighboring tapered tubes 339.

FIG. 11G illustrates still a further embodiment of a segment 334g having a volume of adsorbent processing medium beads 337 that are not segregated into axial flow paths and radial flow paths. Accordingly, the process fluid flow 305 can be directed in a radial direction in the first region 312a (FIG. 3), and the regeneration fluid can be directed in an axial direction in the third region 312c (FIG. 3). Because this arrangement does not segregate the process fluid from the regeneration fluid, there will be mixing of these fluids and the purification efficiency of the arrangement is expected to be lower than the arrangements described above with reference to FIGS. 11A-11F.

One feature of the arrangements described above with reference to FIGS. 11A-11F is that they include a large amount of surface area per unit volume and accordingly have a high heat transfer effectiveness. In particular embodiments, these arrangements are expected to have specific areas in the range of 4,000-5,000 $m^2/m^3$ and/or an NTU (number of heat transfer units) in the range of 200 to 500. As a result, the regenerative heat transfer fluid can efficiently transfer heat to the adsorbent processing medium 341 during a hot regeneration process, and from the adsorbent processing medium 341 during a cold regeneration process. An advantage of this arrangement is described below with reference to FIG. 12.

Figure 12:
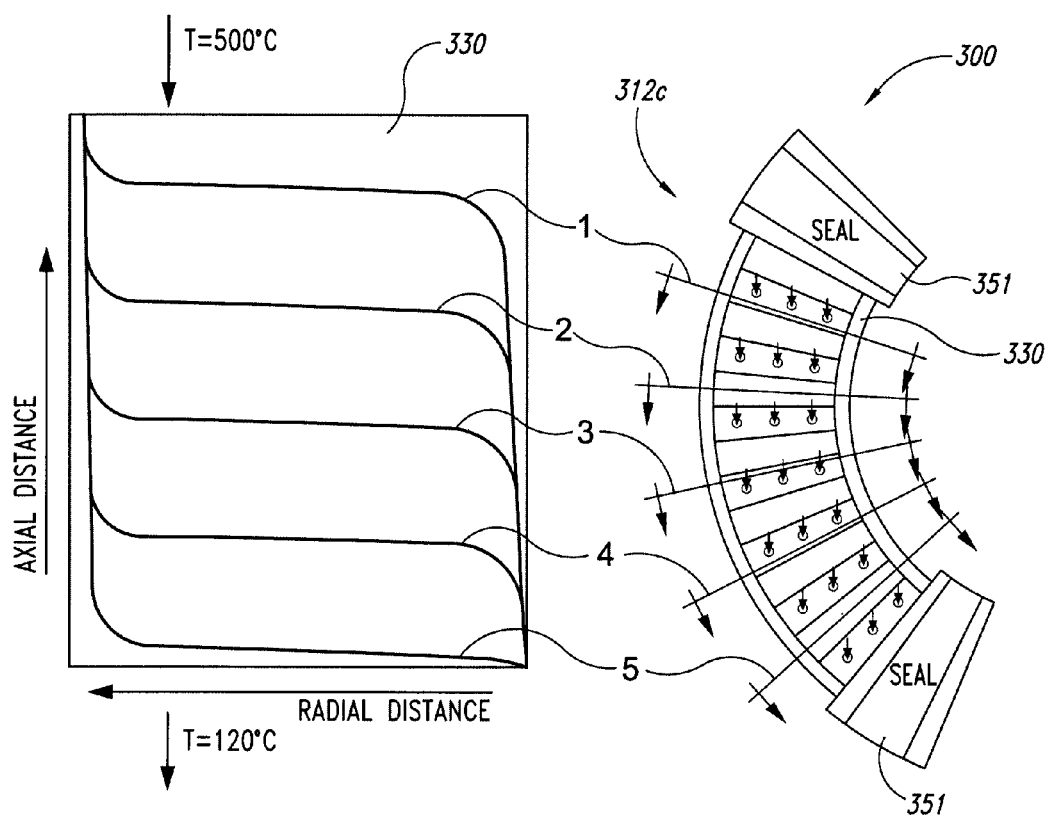
FIG. 12 is a graphical illustration of the temperature performance characteristics of an adsorbent heat transfer element configured in accordance with an embodiment of the disclosure.

FIG. 12 shows a representative third region 312c of the system 300 described above with reference to FIG. 3, along with temperature profiles taken at a variety of circumferential locations within the third region 312c. In a particular embodiment, hot gas is supplied in an axially downward direction at about 500° F. Due to the large surface area in the heat/mass transfer element 330, the gas exits the heat/mass transfer element 330 at about 90° F. within the third region 312c until just before the segment exits the third region 312c. FIG. 12 illustrates the temperature profiles e.g., the temperature front or boundary above which temperatures are about 500° F. and below which temperatures are at about 90° F. As shown in FIG. 12, the temperature front is quite sharp and quite flat, characteristic of excellent heat transfer between the hot regeneration fluid and the heat/mass transfer element 330. Accordingly, the adsorbent processing medium of the heat/mass transfer element 330 is at a uniformly high temperature as it exits the third region 312c, and the heat transfer gas exiting the third region 312c does not undergo a significant temperature rise except near the end of the third region 312c. For example, the average temperature of the total collective heat transfer gas exiting the manifold over the third region 312c can be about 120° F. This sharp heat transfer wave propagating during the regeneration process significantly reduces the amount of cooling that must be provided to the heat transfer gas prior to introducing the cold regenerative heat transfer gas at the fourth region 312d (FIG. 3) e.g., at a temperature of about 68° F. to cool the heat/mass transfer element 330. Similarly, the high surface area of the heat/mass transfer element 330 causes the regenerative heat transfer gas to come out of each segment of the wheel at about 500° F. except near the exit of the fourth region such that the average temperature out of the manifold over the fourth region 312d of the housing is about 450° F., significantly reducing the heating requirements for the regeneration fluid heat exchanger 377 and trim heater 377a (FIG. 3), which increases the temperature of the heat transfer gas to about 500° F. before it re-enters the third region 312c. Accordingly, the majority of the hot and cold thermal energy required for regeneration of the adsorbent is recycled through the system 300 to significantly improve the overall thermal efficiency of the temperature swing adsorption purifier system.

From the foregoing, it will be appreciated that specific embodiments of the disclosure have been described herein for purposes of illustration, but that various modifications may be made without deviating from the disclosure. For example, several aspects of the disclosure were described in the context of processing methane to remove carbon dioxide. In other embodiments, similar systems and methods can be used to process other gases. In addition, the processes undergone by those gases need not be limited to absorption or impurity removal processes. For example, the adsorbent processing medium described above can be replaced with a processing medium having a catalyst that initiates a reaction in the process gas. One such reaction can include the combination of methane with oxygen to form carbon dioxide and water. In still further embodiments, additional heat transfer aspects can be added to the system, for example, to further cool the adsorbent processing medium (and increase its adsorptivity) before it passes into the first region described above. In particular embodiments, the radial and/or axial flow passages or paths are distributed uniformly around the heat transfer elements, and in other embodiments, the axial and/or radial flow passages/paths can be distributed non-uniformly.

In still further embodiments, the system need not include an adsorbent processing medium at all, and can instead perform processes entirely on the basis of heat transfer. For example, the heat/mass transfer element can be replaced with a heat transfer element that is cooled to cryogenic temperatures at the fourth region, and that can remove carbon dioxide from a methane gas stream by causing the carbon dioxide to precipitate and freeze on the walls of the radial (or axial) flow passages. At the third region, the carbon dioxide can be driven (e.g., sublimated) from the heat transfer element by heating the heat transfer element as discussed above. In particular embodiments, the radial and/or axial flow passages or paths are distributed uniformly around the heat transfer element, and in other embodiments, the axial and/or radial flow passages/paths can be distributed non-uniformly. More generally, the heat/mass transfer element can be replaced with an element that performs either heat transfer or mass transfer but not necessarily both.

Certain aspects of the disclosure described in the context of particular embodiments may be combined or eliminated in other embodiments. For example, certain embodiments need not include a closed loop heat exchanger arrangement, and/or need not include a purge zone. Several embodiments were described above in the context of process fluids and heat transfer fluids that include gases. In other embodiments, the process fluids and/or the heat transfer fluids can include liquids. Further, while advantages associated with certain embodiments have been described in the context of those embodiments, other embodiments may also exhibit such advantages. Not all embodiments needs necessarily exhibit such advantages to fall within the scope of the present disclosure. Accordingly, the disclosure and associated technology can encompass other embodiments not expressly described or shown herein.

What is claimed is:

1. A method for processing a gas, comprising:
at a first region, directing a process gas through an adsorbent processing medium along one of a radial axis and an axial axis;
rotating the adsorbent processing medium about a rotation axis from the first region to a third region and directing a heat transfer fluid along the other of the radial axis and the axial axis to be in thermal contact with the adsorbent processing medium at the third region;
rotating the adsorbent processing medium about the rotation axis from the third region to a second region and directing a purge fluid through the adsorbent processing medium along the one of the radial axis and the axial axis at the second region;
rotating the adsorbent processing medium about the rotation axis from the second region to a fourth region and directing the heat transfer fluid along the other of the radial axis and the axial axis to be in thermal contact with the adsorbent processing medium at the fourth region; and
rotating the adsorbent processing medium about the rotation axis from the fourth region to the first.

2. The method of claim 1 wherein rotating the adsorbent processing medium includes rotating the adsorbent processing medium in a generally continuous manner.

3. The method of claim 1 wherein directing a heat transfer fluid includes directing a heat transfer fluid that includes the process gas as a constituent.

4. The method of claim 1, further comprising simultaneously maintaining portions of the adsorbent processing medium at the first, second, third and fourth regions at approximately the same pressure.

5. The method of claim 4 wherein the pressure is from about 80 psi to about 150 psi.

6. The method of claim 1, further comprising equalizing a pressure difference between the third and second regions, caused by different temperatures in the third and second regions, by allowing a controlled amount of fluid to pass between the third and second regions.

7. The method of claim 1, further comprising equalizing a pressure difference between the first and fourth regions, caused by different temperatures in the first and fourth regions, by allowing a controlled amount of fluid to pass between the first and fourth regions.

8. The method of claim 1 wherein directing the process gas through the adsorbent processing medium includes directing a methane-containing process gas through the adsorbent processing medium to remove impurities from the methane.

9. The method of claim 1 further comprising exposing the adsorbent processing medium to environments in individual ones of the regions for different periods of time, while rotating the adsorbent processing medium at a generally constant rate.

10. A method for processing a gas, comprising:
rotating an adsorbent-containing heat/mass transfer element about a rotation axis to sequentially expose a portion of the heat/mass transfer element to multiple processing regions;
at one of the processing regions, directing a first fluid through the portion of the heat/mass transfer element in one of an axial direction and a radial direction while preventing the first fluid from passing through the portion of heat/mass transfer element in the other of the axial direction and the radial direction at the one processing region; and
at another of the processing regions, directing a second fluid through the portion of heat/mass transfer element in the other of the axial direction and the radial direction while preventing the second fluid from passing through the portion of the heat/mass transfer element in the one of the axial direction and the radial direction at the other processing region.

11. The method of claim 10 wherein directing a first fluid includes directing methane in the radial direction to adsorb impurities in the methane to the heat/mass transfer element, and wherein directing a second fluid includes directing a heat transfer fluid in the axial direction to desorb the impurities.

12. The method of claim 10 wherein directing the heat transfer fluid includes directing a heat transfer fluid that includes methane.

13. The method of claim 10 wherein directing the heat transfer fluid includes collecting the heat transfer fluid after desorbing the impurities, and cooling the adsorbent heat/mass transfer element with collected heat transfer fluid.

14. The method of claim 10 wherein:
the processing regions include first, second, third and fourth processing regions positioned circumferentially around the rotation axis;
directing a first fluid includes directing methane in the radial direction at the first region to adsorb impurities in the methane to the heat/mass transfer element;
directing a second fluid includes directing a heat transfer fluid in the axial direction at the third region to desorb the impurities, and wherein the method further comprises:
purging the heat/mass transfer element by directing a purge gas through the heat/mass transfer element in the second region;
cooling the heat/mass transfer element by collecting the heat transfer fluid at the third region after desorbing the impurities, and directing the heat transfer fluid through the heat/mass transfer element at the fourth region;
at least partially equalizing pressures between the second and third regions by allowing methane from the third region to flow toward and mix with purge gas at the second region; and
at least partially equalizing pressures between the first and fourth regions by allowing methane from the first region to flow toward and mix with heat transfer fluid at the fourth region.

* * * * *